(12) United States Patent
Walter et al.

(10) Patent No.: US 6,514,963 B2
(45) Date of Patent: Feb. 4, 2003

(54) METHODS FOR THE INHIBITION OF EGG PRODUCTION IN TREMATODES

(75) Inventors: Mark Walter, Sebastopol, CA (US); Armand Kuris, Santa Barbara, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/908,676

(22) Filed: Jul. 18, 2001

(65) Prior Publication Data

US 2002/0111342 A1 Aug. 15, 2002

Related U.S. Application Data

(60) Provisional application No. 60/219,035, filed on Jul. 18, 2000.

(51) Int. Cl.[7] ................... A61K 31/554; A61K 31/277; A61K 31/454; A61K 39/108; A01N 25/32
(52) U.S. Cl. ................. 514/211.07; 514/371; 514/274; 514/183; 514/207; 514/277; 514/588; 514/595; 514/744; 514/758; 514/759; 514/841; 514/885; 514/893; 514/946; 424/405; 424/406; 424/151.1; 424/265.1
(58) Field of Search ............................ 514/211.07, 371, 514/274, 183, 207, 277, 588, 595, 744, 758, 759, 841, 885, 893, 946; 424/405, 406, 151.1, 265.1

(56) References Cited

U.S. PATENT DOCUMENTS

| | | | | |
|---|---|---|---|---|
| 5,856,348 A | * | 1/1999 | Rossignol | 514/371 |
| 6,143,752 A | * | 11/2000 | Oren | 514/274 |

OTHER PUBLICATIONS

Katsumata et al., Hatching of *Schitosoma mansoni* eggs is a Ca 2+/calmodulin–dependent process, 1989, Parasitology Research, 76:90–91.*

* cited by examiner

*Primary Examiner*—Frederick Krass
*Assistant Examiner*—Clinton Ostrup
(74) *Attorney, Agent, or Firm*—Townsend and Townsend and Crew LLP

(57) ABSTRACT

The present invention comprises methods and compositions for use in inhibiting egg production by parasitic trematode worms comprising administering to an individual in need thereof an effective amount of an agent which transiently inhibits the influx of calcium through a cell membrane calcium channel. Inhibition of egg production in the worms ameliorates many of the symptoms and pathology related to infection by trematode related diseases, including Schistosomiasis. The methods can also effect disease transmission by reducing the number of eggs released into the environment available to continue the worm life cycle.

14 Claims, 4 Drawing Sheets

METHODS FOR THE INHIBITION OF EGG PRODUCTION IN TREMATODES

CROSS-REFERENCES TO RELATED APPLICATIONS

This application claims priority from Provisional Application U.S. Serial No. 60/219,035, filed on Jul. 18, 2000, the disclosure of which is incorporated herein by reference.

BACKGROUND OF THE INVENTION

Parasitic worms of the family Trematoda, including the genus Schistosoma (e.g., S. mansoni, S. haematobium, S. japonicum, and the like) and Echinostoma are the causative agents of mammalian disease. In particular, Schistosoma worms are responsible for human schistosomiasis. Worldwide approximately 200 million people are actively infected, with an additional 500–600 million at risk. A large number (more than 20 million) of those infected show severe chronic illness, resulting from damage to various organ systems including the liver, bladder, heart, lungs, spleen, and intestine.

Schistosoma are a blood fluke which inhabit the vasculature serving the liver, bladder, intestine and spleen of a human host. A mating pair of the worms live from several to more than 30 years wherein they can continuously shed from 300 to more than 3000 eggs per day. The adult worms do not reproduce themselves within the human body. The eggs of these worms leave the body of an infected individual through the urine and feces. If they reach water, they hatch into a first larval stage, or miracidia. The miracidia, which are completely formed within the eggs, resemble ciliates. They must reach their freshwater snail host within a few hours to survive. If they reach their host, they develop into sporocysts. The sporocysts divide asexually to give rise to daughter sporocysts, and the daughter sporocysts in turn give rise to cercariae, a tadpole-like larval stage. A single infected snail can release 100,000 cercariae during its lifetime of several months. The cercariae of Schistosoma burrow into human skin, ultimately reaching the bloodstream where they are swept into the lungs. Subsequently, the cercariae mature and pair during their migration to the veins which supply the upper intestine, the lower intestine, the liver, or the bladder, depending on the species of Schistosoma involved.

Pathogenesis of schistosomiasis is not due to the presence, nor the blood feeding of the adult worms, but, rather, results from an immune reaction to the large number of eggs produced and released by the female worms. A large percentage of these eggs become trapped in various tissues (liver, spleen, etc.) with resultant inflammation and granuloma formation. The remainder of the eggs pass through intestinal or bladder tissues and are released into the environment, which is essential for continuation of the schistosome life cycle and disease transmission.

Currently there are only three drugs used in chemotherapy of schistosomiasis. These include metrifonate (Trichlorfon; (2,2,2-trichloro-1-hydroxyethyl)-phosphonic acid dimethyl ester), oxamniquine (1,2,3,4-tetrahydro-2-[[(1-methylethyl)amino]methyl]-7-nitro-6-quinolinemethanol), and praziquantel (2-(cyclohexylcarbonyl)-1,2,3,6,7,-11b-hexahydro-4H-pyrazino[2,1-a]isoquinolin-4-one). All three drugs are effective to varying degrees and can eliminate adult worms from the human host. Praziquantel is the current drug of choice and has been used successfully worldwide against all three species of schistosomes. It has been suggested that praziquantel functions by causing exposure of normally hidden worm surface proteins and glycoproteins to the host immune system. Some or all of these surface "antigens" may not be essential for worm survival, and a decrease in their production and/or use by schistosomes could be driven by praziquantel treatment. If so, resistance to praziquantel would be expected to increase in the future driven by the repeated dosing of praziquantel practiced in some endemic areas. In fact, there is increasing evidence of emergence of praziquantel resistant strains of S. mansoni in certain regions of the world. Such reports are particularly disturbing because metrifonate is only effective against S. haematobium infections, and S. mansoni resistance to oxamniquine has previously been reported.

Chemotherapy with each of these drugs only seeks to eliminate the adult worms in an infected individual. Removal of the adult worm does not confer protection against reinfection. Since reinfection occurs frequently in endemic areas, praziquantel and the other anti-schistosomal agents must be used repeatedly to control the disease, thereby increasing the pressure for continued emergence of drug resistance and increasing the cost of treatment.

In light of the increasing reports of drug resistance, new avenues of chemotherapeutic control of schistosomiasis are needed. At present, there is little work being done to identify new agents with antischistosomal properties, and most work has yet to progress past initial testing in a mouse model. The bulk of the current research effort to control human schistosomiasis is devoted to construction of an anti-schistosomal vaccine. Development of an effective vaccine against schistosomiasis would be of enormous benefit because of its potential to prevent infection. However, no vaccine affording such protection has yet been achieved despite nearly two decades of work. Further, there are major economic and logistical problems to effectively deploying a modern vaccine in the developing countries where schistosomiasis is endemic.

Surprisingly, the present invention provides methods and compositions for the inhibition of egg production by adult Trematoda worms. In particular, methods for the inhibition of egg production by Schistosoma, Echinostoma and Fasciola worms. The inhibition of egg production, in addition to reducing or eliminating pathology related to infection of the host, also reduces (or possibly eliminates) the release of Trematoda eggs into the environment to continue the worm life cycle. By reducing the number of eggs released into the environment the method of the present invention provides a means to effectively reduce the rate of reinfection of the mammalian host.

SUMMARY OF THE INVENTION

The purpose of the invention described herein is to provide a method for inhibiting the production of eggs from parasitic trematode worms by administering an agent which transiently inhibits the function of calcium channels. The methods can be used to treat, for example, schistosomiasis, and to inhibit both the pathology and transmission of schistosomiasis in humans.

Many of the agents effective in the methods of the present invention comprise compounds that are used currently in the treatment of hypertension, arrhythmias, angina and other cardiovascular diseases. Generally, all of the agents useful in the methods of the present invention should be capable of transiently blocking the influx of extracellular calcium through calcium channels in the plasma membrane of a wide variety of cells. In particular, agents effective in the methods of the present invention comprise molecules which comprise dihydropyridine, phenylalkylamine, benzothiazepine, diphenylbutylpiperdine or flunarizine/cinnarizine compounds, and the like. Of particular interest are the commonly prescribed calcium channel blockers verapamil, nifedipine, diltiazem, and nicardipine.

DESCRIPTION OF THE SPECIFIC EMBODIMENTS

Figure 1A:
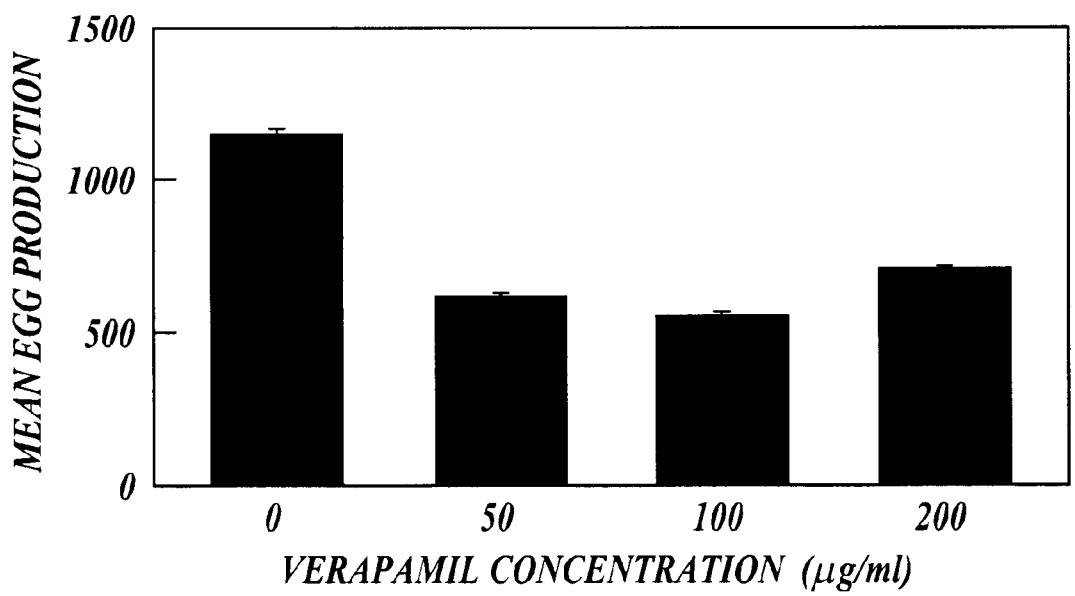
FIGS. 1A and 1B depict the effect of elevated (FIG. 1A) and therapeutic (FIG. 1B) concentrations of verapamil on the mean egg produced of Echinostoma caproni as compared to controls.

Production of eggs by adult female schistosomes is responsible for both the pathology of schistosomiasis and continuation (transmission) of the parasite lifecycle (von Lichtenberg, in, *The Biology of Schistosomes: From Genes to Latrines,* Rollinson and Simpson eds., Academic Press, pp 185–224 (1987), Warren et al., *Am. J. Pathol.* 51:735–756 (1967), Warren, *Nature* 273:609–612 (1978), Wyler, *Parasitology Today* 8:277–279 (1992)). The pathways leading to the production of viable eggs by schistosomes, and by digenetic trematodes in general, are thought to include synthesis of and storage of eggshell proteins (EP) in vitelline cells, exocytosis of EP from the vitelline cells, and crosslinking of EP into eggshell by phenol oxidase activity (Basch *Schistosomes: Development, Reproduction and Host Relations,* Oxford University Press (1991), Cordingley, *Parasitology Today* 3:341–344 (1987), Eshete and LoVerde, *J. Parasit.* 79:309–317 (1993), Nollen, *Exp. Parasit.* 30:64–67 (1971), Smyth and Clegg, *Exp. Parasit.* 8:286–323 (1959), Wharton, *Parasitology* 86:85–97 (1983)). Although these events have been documented, their regulation is not well understood. However, some evidence suggests that calcium is involved in regulation of schistosome reproduction.

Exocytosis by vitelline cells of *Schistosoma mansoni* was shown to be dependent on the entry of extracellular calcium. An increased calcium influx, induced by treatment of worms in vitro with the calcium ionophore A23187, resulted in exocytosis of EP (Wells and Cordingley, *Exp. Parasit.* 73:295–310 (1991), incorporated herein by reference). Conversely, chelation of extracellular calcium with EGTA has been found to prevent release of egg proteins (Wells and Cordingley, (1991) supra). Further, a number of calcium binding proteins (CBP) have been identified in schistosome tissues, including those of the reproductive system, suggesting a role for calcium in the function of those tissues (Fuhrman, *Parasitology Today* 6:172–173 (1990), Havercroft et al., *Mol. Biochem. Parasit.* 38:211–220 (1990), Hawn et al., *J. Biol Chem.* 268:7692–7698 (1993), Khalife et al., *Parasitology* 108:527–532 (1994), each incorporated herein by reference in their entirety). Importantly, calmodulin (CaM) has been identified as one of these schistosome calcium binding proteins (Fuhrman, *Parasitology Today* 6:172–173 (1990), Siddiqui et al., *Exp. Parasit.* 72:63–68 (1991), Thompson et al., *Am. J. Parasit.* 251:R1051–R1058 (1986)).

Calmodulin is an ubiquitous CBP found in a wide variety of organisms and tissues, and functions to translate changes in the cytoplasmic calcium concentration into regulation of numerous cellular processes, including muscle contraction, cell division and enzyme activity (Cheung, *Science* 207:19–27 (1980), Klee and Vanaman *Adv., Protein Chem.* 35:213–321 (1982), Pallen et al., *BioEssays* 2:113–117 (1985), Veigl et al., *Biochem. Biophys. Acta* 738:21–48 (1984)). Similarly, it has been demonstrated that CaM isolated from *Schistosoma mansoni* stimulates the in vitro activity of bovine brain phospodiesterase supporting a role for schistosome CaM in regulation of enzymatic activity (Thompson et al., *Am. J. Parasit.* (1986), supra). Taken together, the above evidence supports a role for calcium in the regulation of reproduction in Trematode worms including Schistosoma, Echinostoma and Fasciola.

In most organisms, entry of calcium is restricted primarily to gated membrane channels (Hosey and Lazdunski, *J. Mem. Biol.* 104:81–105 (1988)). However, little work has been done to specifically identify and characterize putative calcium channels of the schistosome tegument and other membranes. The existence of such channels can be inferred from studies showing that agents known to specifically block the voltage-dependent L-type calcium channels of mammalian cells (calcium channel blockers, CCBs) also inhibit the calcium-dependent contraction of muscle in schistosomes (Blair et al., *Exp. Parasit.* 78:302–316 (1994), Soares de Moura et al., *Exp. Parasit.* 63:173–179 (1987)). Further, the calcium-dependent contractions of muscle in *F. hepatica* were shown to be inhibited in vitro by the CCB nifedipine (Graham et al., *Am. J. Physiol.* 277:R374–R383 (1999)). If these channels function as a primary route of calcium entry in Trematoda worms, particularly Schistosoma species, they could represent both a major source of calcium for reproductive processes and a convenient, externally-directed site for pharmacological intervention.

Therefore, although calcium has been implicated in production of the eggshell and in metabolism of the developing embryonic tissues of the worm (Wells and Cordingley, *Exp. Parasit.* 73:295–310 (1991)), there is however, no suggestion or disclosure in the art that compounds which transiently inhibit calcium influx through calcium channels might be potentially useful as a means for the treatment of pathology associated with a trematode infection, including schistosomiasis. Additionally, it is known that blockade of calcium ion influx using a compound which inhibits or blocks the calcium channel function eliminates contractile activity of the body-wall musculature of adult worms (Miller et al., *Exp. Parasit.* 84:410–419 (1996); Day et al., *Parasitology* 108:425–432 (1994)).

There are five main types or classes of calcium channels found in the membrane of cells designated L, N, T, P and Q. Different tissues can be characterized by the type and combination of calcium channels present. Cardiac, skeletal, and smooth muscle cells typically have L and T channels. Different neurons and other cells of the nervous system have varying combinations of all five channel types, and N channels are characteristic of all neural tissues. In schistosomes, the walls of the body, gut and reproductive system structures are largely composed of smooth muscle. The cells of these tissues would therefore likely have calcium channels similar to, or identical with, L and T channels on their surfaces which are exposed to the environment (the host blood supply) and accessible to drugs administered systemically to the host.

Compounds which transiently inhibit calcium influx through calcium channels useful in the present invention include many of those which are currently used therapeutically in mammals to treat hypertension, arrhythmias, angina and other cardiovascular diseases. There are three main classes of compounds which are used therapeutically in mammals as calcium channel blockers. They include dihydropyridines (e.g., nifedipine (1,4-dihydro-2,6-dimethyl-4-(2-nitrophenyl)-3,5-pyridinedicarboxylic acid dimethylester), nicardipine (1,4-dihydro-2,6-dimethyl-4-(3-nitrophenyl)-3,5-pyridinedicarboxylic acid methyl 2-[methyl-(phenylmethyl)amino]ethyl ester), and the like); phenylalkylamines (e.g., verapamil (α-[3-[[2-(3,4-dimethoxyphenyl)ethyl]methyl-amine]propyl]-3,4-dimethoxy-α-(1-methylethyl)-benzeneacetonitrile), and the like); and benzothiazepines (e.g., diltiazem (3,4,5-trimethoxybenzoic acid (tetrahydro-1H-1,4-diazepine-1,4 (5H)-diyl)di-3,1-propanediyl ester), and the like). Additional examples include nimodipine (1,4-dihydro-2,6-dimethyl-4-(3-nitrophenyl)-3,5-pyridinedicarboxylic acid 2-methoxyethyl 1-methylethyl ester); nitrendipine (1,4-dihydro-2,6-dimethyl-4-(3-nitrophenyl)-3,5-pyridinedicarboxylic acid ethyl methyl ester); amlodipine besylate (2-[(2-aminoehoxy)methyl]-4-(2-chlorophenyl)-1, 4-dihydro-6-methyl-3,5-pyridinedi-carboxylic acid 3-ethyl 5-methyl ester); bepridil (β-[(2-methylpropoxy)methyl]-N-phenyl-N-(phenylmethyl)-1-pyrrolidineethanamine); the diphenylbutylpiperidines (e.g., pimozide (1-[1-[4,4-bis(4-fluorophenyl)butyl]-4-piperidinyl]-1,3-dihydro-2H-benzimidazol-2-one), fluspirilene (8-[4,4-bis(4-fluorophenyl)butyl]-1-phenyl-1,3,8-trizaspiro[4.5]decan-4-one), and the like); and agents belonging to the flunarizine ((E)-1-[bis(4-fluorophenyl)methyl]-4-(3-phenyl-2-propenyl)piperazine)/cinnarizine (1-(diphenylmethyl)-4-(3-phenyl-2-propenyl)piperazine) series of compounds. All of these compounds target the L channel with very little or no effect on other channel types. Further, these compounds are much more effective in blocking an L channel on smooth muscle and cardiac (myocardial) muscle cells than on nerve tissues. Therefore, the primary effect of these compounds when used therapeutically in a mammal are on the cardiovascular system. The blockade of L channels by the compounds useful in the methods of the present invention is rapidly reversible. The compounds are typically metabolized to inactive molecules as they "pop off" the channels.

Other compounds are known to specifically block calcium channels. These compounds include a number of spider toxins isolated from, for example, funnel web spiders and a species of tarantula. Tunnel web toxin (FTX) typically blocks, for example, N, P and T channels, but not L channels (Osvaldo, *Toxicon* 35:1161–1191 (1997)). The w-agatoxins, also isolated from the funnel web spider, comprise four subtypes. Most of these toxins block only N channels (Osvaldo, supra, (1997)). Although, type IIIA toxin also blocks some L channels found on certain types of nerve cells. While w-gamma toxin isolated from the tarantula blocks N, P and Q channels (Osvaldo, supra, (1997)). These spider toxins specifically block calcium channels of neural tissue, not muscle, so their overall systemic effects are primarily on the nervous system.

In particular, the spider toxins are known to inhibit neurotransmitter release, which results in no transmission of nerve impulses and/or muscle paralysis, and inhibition of the secretion of certain compounds (hormones) from neural type tissues, e.g., epinephrine and norepinephrine, and the like. The binding of spider toxins to calcium channels is often reversible, but typically, only slowly and therefore the compounds are more toxic than those compounds which transiently block calcium channel function used therapeutically in mammals.

As used herein, the terms "treatment" or "treating" include: (1) preventing undesirable symptoms or pathological states from occurring in a subject who may be predisposed to these undesirable symptoms or pathological states but who has not yet been diagnosed as having them; (2) inhibiting undesirable symptoms or pathological states, i.e., arresting their development; or (3) ameliorating or relieving undesirable symptoms or pathological states, i.e., causing regression of an undesirable symptom or of a pathological state. Any amount of an agent of the invention which accomplishes any of these goals is termed an "effective amount", and intended to include both prophylactic and therapeutic uses of the agents.

The calcium channel blocking agents effective in the methods of the invention are also useful in the prevention or treatment of diseases or pathological states benefiting from the inhibition of egg production from trematodes. Further, by reducing egg production in the adult worm fewer eggs pass through the host and are released into the environment. This in turn reduces the number of infected intermediate host animals and therefore can reduce the rate of release of infectious larvae and the rate of reinfection of the mammalian host.

Also, unlike compounds that remove adult worms from the host, the methods of the present invention not only can potentially decrease the number of eggs entering the environment to carry on the life cycle of the worms, but the presence of the adult worms in the host can induce an immune response to potential super infections, i.e., infection by additional worms. In the adult host worms are present in the blood stream where the external antigens of the worm can be recognized by the immune system of the host. The antibody and cell mediated immunity induced by the presence of the adult worms can prevent any additional worms which enter the body from infecting the host.

The calcium channel blockers or other compounds useful in the present invention can be incorporated as components of pharmaceutical compositions containing a therapeutic or prophylactic amount of at least one calcium channel blocker with a pharmaceutically effective carrier. In preparing the pharmaceutical compositions useful in the present methods, a pharmaceutical carrier can be employed which is a compatible, nontoxic substance suitable to deliver the calcium channel blocker or therapeutic compound identified in accordance with the methods disclosed herein to a patient. Sterile water, alcohol, fats, waxes, inert solids and even liposomes can be used as the carrier. Pharmaceutically acceptable adjuvants (buffering agents, dispersing agents) can also be incorporated into the pharmaceutical composition.

The agents which block calcium channels and pharmaceutical compositions thereof are particularly useful for oral administration, but can also be administered parenterally, i.e., intravenously, intra-arterially, intramuscularly, or subcutaneously. Typically, the compounds of the present invention are given orally and injection is not required. Administration of the compounds is commonly prophylactic, i.e., a daily basis, to stabilize or alleviate chronic conditions. Actual methods for preparing administrable compositions will be known or apparent to those skilled in the art and are generally described in more detail in, for example, *Remington's Pharmaceutical Science,* 17th Ed., Mack Publishing Co., Easton, Pa. (1985), which is incorporated herein by reference.

Commonly, calcium channel blockers used to treat cardiovascular conditions are administered orally at a therapeutic dosage of about 30 mg/day to about 500 mg/day. In particular, verapamil, for example, is administered at about 80 mg/day to 480 mg/day, nifedipine at about 30 mg/day to about 120 mg/day, nicardipine at about 60 mg/day to 120 mg/day, and diltiazem at 90 to 360 mg/day. All of the calcium channel blockers used therapeutically today are metabolized by enzymes in the liver after absorption from the intestine into the blood. The actual amount of active drug in the blood of a patient left after the initial metabolism, $C_{max}$ (maximal steady state plasma concentration) for the calcium channel blockers provided above are as follows: verapamil about 30 ng/ml to about 330 ng/ml, nifedipine about 40 ng/ml to about 130 ng/ml, nicardipine about 40 ng/ml to about 140 ng/ml and diltiazem about 200 ng/ml to about 300 ng/ml.

The concentration of compounds used in the methods of the present invention will depend on the state of the patient and the judgment of the treating physician. Nevertheless, it is likely that the compounds will be administered such that the $C_{max}$ will be no more than about 500 ng/ml. The dosage selected will produce an effective concentration of between about 30 ng/ml to about 500 ng/ml. More specifically the dosage will produce an effective concentration of between about 30 ng/ml to about 150 ng/ml. The dosage actually administered to result in the desired $C_{max}$ will also depend on the particular mode of administration selected.

The compounds of the invention useful in inhibiting Trematoda egg production can be administered for prophylactic or therapeutic treatment. In one particular embodiment of the present invention, treatments intended for prophylactic applications, the compositions are administered to a patient likely to be exposed to Schistosoma larval stages. Typically, those areas where risk of transmission is greatest and prophylactic use can be of the greatest benefit include Africa, parts of the Middle East (particularly Iraq and Iran), scattered localities throughout Asia (China, Philippines, Thailand, Indonesia, and Vietnam), northeastern South America and some Caribbean islands. The potential patient population for prophylactic treatment includes, but is not limited to, individuals living in the geographic regions at high risk for transmission. In these populations, children are at the greatest risk. In addition, international as well as local government and non-government organization aid workers, tourists and travelers, are also at risk in these areas. Military personnel are also at risk in regions of transmission of schistosomiasis.

Administration of the compounds of the invention can be carried out prior to exposure to the worm antigen or antigens or at the same time. To prevent recurrent disease and the sequelae thereof, the compositions can be administered daily, weekly or other scheduled maintenance therapy. The regimen will also depend on the dosage and effectiveness thereof, the intended use, and the patient's general state of health. The treating physician, or other health professional can select dose levels and a pattern of administration, i.e., route of administration and single or multiple dosage administrations required for successful prophylactic treatment.

In therapeutic applications, the compounds of the invention are typically administered to a patient already suffering from undesirable symptoms or pathology of Trematoda infection, particularly Schistosoma infection, in an amount sufficient to at least partially suppress the production of worm eggs. An amount of calcium channel blocking agent adequate to accomplish this is defined as a "therapeutically effective dose."Amounts effective for this use will depend upon the compound being employed, the route of administration, the severity of the undesirable symptoms or pathological state, and the general state of the patient's health. Determination of an effective amount of a compound of the invention to suppress the production of eggs can be determined by techniques well known in the art. For example, a decrease in egg-specific immunoglobulin or reduced inflammatory response and thus efficacy of the subject compositions, can be monitored with a variety of well known in vitro diagnostic procedures.

In another embodiment, the invention provides a formulation of a calcium channel blocker which effectively inhibits egg production of the parasitic fluke, *Echinostoma caproni*. Worms of the Echinostoma group are closely related biologically to the schistosomes, and share the same mechanisms of egg production. In fact, the biochemical process of forming eggs in the large group of worms known as trematodes, which includes the schistosome and echinostome worms, (among others) is very similar, and may be identical. The same key enzyme, phenol oxidase, is used by all trematodes studied to make an egg shell. Further, the steps for yolk formation and secretion, production and secretion of egg shell materials, and packaging of the embryo into the egg are similar in all trematodes studied. Methods and compositions used to reduce or prevent egg production in one type of trematode are likely to function in another. It is also likely that the sensitivity of each species of trematode to each calcium channel blocking agent will be different due to differences in structure and coating of the body wall and size of the worm, and also the type and density of calcium channels on different worms will likely differ. It is therefore likely that the $C_{max}$ required to prevent egg production for one species will differ from that required for another species. Methods are well known for determining the concentration of an agent required for a prophylactic or therapeutic dose.

In another specific embodiment of the present invention in vitro methods are provided for the determination of the $C_{max}$ value of an agent which transiently inhibits calcium channel function required to inhibit egg production in various species of trematode worms. In particular, the effect of a calcium blocking agent can be tested in a system biased against seeing a positive effect. For example, in one embodiment of the present invention the amount of calcium in the in vitro medium exceeded the amount of calcium needed to inhibit the in vitro binding activity of the agent being tested by 50%. Therefore, at lower therapeutic concentrations of the agent being tested it would be likely that the agent would compete with, and be inhibited by, calcium for transport into a cell through a calcium channel. In this particular embodiment, it was also assumed that the worms would not metabolize and inactivate the calcium channel blocking agent tested, and that the agent would not be adsorbed by culture dishes, components of the culture medium, or by various molecules of the worm itself.

In a particular example of this embodiment, the calcium channel blockers verapamil, diltiazem, and nifedipine were found to be effective in inhibiting *Schistosoma mansoni* and *Echinostoma caproni* egg production. The concentration of active drug necessary (in particular, nifedipine) to obtain an effect against *Echinostoma caproni* was discovered to be in the concentration range of drug found to be effective in currently approved therapies for cardiac use.

Calcium channel blockers as above can also be used in therapeutic approaches to treating schistosomiasis to reduce or eliminate the pathology-inducing effects of the schistosome eggs. In particular, the methods can be effective in situations where exposure to reinfection is a frequent risk. High risk of reinfection is a common circumstance in many regions of the world where schistosomiasis is prevalent. This approach would preserve the partial protection of concomitant immunity and decrease parasite transmission to the snail intermediate hosts.

Calcium channel blockers can also be used as a long-term treatment against the pathology-inducing effects of schistosome eggs, especially where individuals or populations have been shown to be developing resistance to current drug therapies including praziquantel, oxamniquine and/or metrifonate. Further, the methods of the present invention are particularly useful for treatment of patients or populations with demonstrated non-compliance with other antischistosomal chemotherapies.

The use of calcium channel blockers to treat schistosomiasis offers a number of advantages to current therapeutic practice. Firstly, praziquantel, oxamniquine and metrifonate can not be used for long-term treatment due to adverse side effects and high cost. In comparison, the demonstrated low incidence of adverse side effects with long-term administration of calcium channel blockers, and their availability at low-cost, suggest that these compounds can be more useful than current therapies for long-term treatment.

Secondly, therapeutic activities of oxamniquine and metrifonate are limited to only one species ($S.$ $mansoni$ and $S.$ $haematobium$ respectively). In comparison, all three species of schistosomes share common mechanisms of egg production, embryo formation and egg release, suggesting calcium channel blockers should show activity against all species.

The presence of non-reproducing (i.e., no egg production) adult worms in the host is potentially beneficial because such worms can afford a measure of protection because they induce concomitant immunity to acquisition of new infections. This is advantageous as it decreases the incidence of superinfection, which leads to more immediate and acute pathology. It also enables the treated humans to act as a population sink for schistosomes, decreasing disease transmission from humans to the intermediate snail hosts, and thus ultimately reducing further risk of transmission to humans. However, the activities of praziquantel, oxamniquine and metrifonate remove the adult worms from the host, which eliminates any potential partial protection of concomitant immunity induced by the adult worm and can allow reinfection with potentially high worm intensities.

In comparison, the beneficial activity of calcium channel blockers does not require the removal of the adult worm. Therefore, it should be possible to deliver an egg production inhibitory dosage of the drug eliminating pathology without killing the adult worm. The continued presence of adult worms in the body of the host, which are incapable of producing a pathological effect, would then provide the added advantage of a concomitant immunity against reinfection. This principle is analogous to replacing the effects of pesticides, which permit pest populations to strongly rebound to new and high levels, with a careful approach that includes a natural control against damaging high pest numbers by introducing via natural enemies.

The following examples are offered by way of illustration, not by way of limitation.

EXAMPLE 1

In this example the intestinal trematode $Echinostoma$ $caproni$ was isolated from infected mice and placed into culture. The worms were treated with various concentrations of a calcium channel blocker and eggs released into the dish and those which remained inside the worm were counted under the varying conditions.

$Echinostoma$ $caproni$ was maintained ex vitro by cycling through albino $Biomphaleria$ $glabrata$ and male Swiss-Webster mice (Charles River) as described in Kuris and Warren ($J.$ $Parasit.$ 66:630–635 (1980)), except that adult worms from these mice were used as a source of eggs to maintain the life cycle. Mice for experiments were infected with approximately 25 to 40 metacercariae (infectious larvae) in water by gastric intubation. About 21 days post infection the mice were euthanized and the intestines were removed and dissected. Adult worms were recovered from 5 infected mice and pooled in a large dish of sterile, 37° C. RPMI-1640 culture medium (Sigma), pH 7.5, supplemented with 100 U/ml penicillin G potassium (Sigma) and 0.2 mg/ml streptomycin sulfate (Fisher). All further procedures were performed under a sterile hood using aseptic technique.

The worms were removed from the wash and visually assessed for viability using a dissecting microscope removing damaged individuals. The worms were further inspected for viability, and noticeably small or large worms were removed. the remaining worms were used as a source for adult worms.

For each experiment, therapeutically-useful concentrations or elevated, non-therapeutic concentrations were tested. Therapeutic concentrations of each calcium channel blocker was based on the normal range of maximum, steady-state plasma concentration ($C_{max}$) shown to be efficacious in human patients. In general the concentrations were in the nanogram range. Elevated concentrations in the microgram range were used to ensure that an effect was not missed due to insufficient drug and/or low channel affinity for the calcium channel blocker being tested. Each tested concentration of drug constituted a treatment group. Stock verapamil and diltiazem were solubilized in culture medium, while nifedipine was solubilized in ethanol. Accordingly, controls consisted of culture medium (verapamil, diltiazem) or culture medium plus ethanol (nifedipine).

Each treatment group of 10 worms was randomly assigned to 10 petri dishes (35×10 mm) each containing 4 ml sterile culture medium. Appropriate volumes of drug stock solution or culture medium were added to the dishes to give final concentrations as follows: elevated verapamil: 0, 50, 100, and 200 µg/ml; therapeutic verapamil: 0, 75, 150, 300, and 600 ng/ml; elevated nifedipine: 0, 25, 50, 100, and 200 µg/ml; therapeutic nifedipine: 0, 40, 80, 120, 160, 400, and 4000 ng/ml; elevated diltiazem: 0, 5, 10, and 50 µg/ml; therapeutic diltiazem: 0, 75, 150, 300, and 600 ng/ml.

All dishes were maintained in a 37° C. incubator in 5% $CO_2$ for approximately 24 hours. Dishes were removed; each worm was visually assessed under a dissecting microscope for viability; and viable worms were transferred to corresponding dishes of ice-cold water to immediately stop egg production and to kill the worms. All dishes were held at 2° C. for analysis.

The eggs released during incubation were counted using a dissecting microscope. Worms were then dissected and the eggs remaining in utero were freed and counted. Total egg production was defined as the sum of the eggs released during incubation plus the eggs retained in utero. The effect of each drug on egg production was analyzed using analysis of variance (ANOVA) on the log transformed data.

Results

Figure 2A:
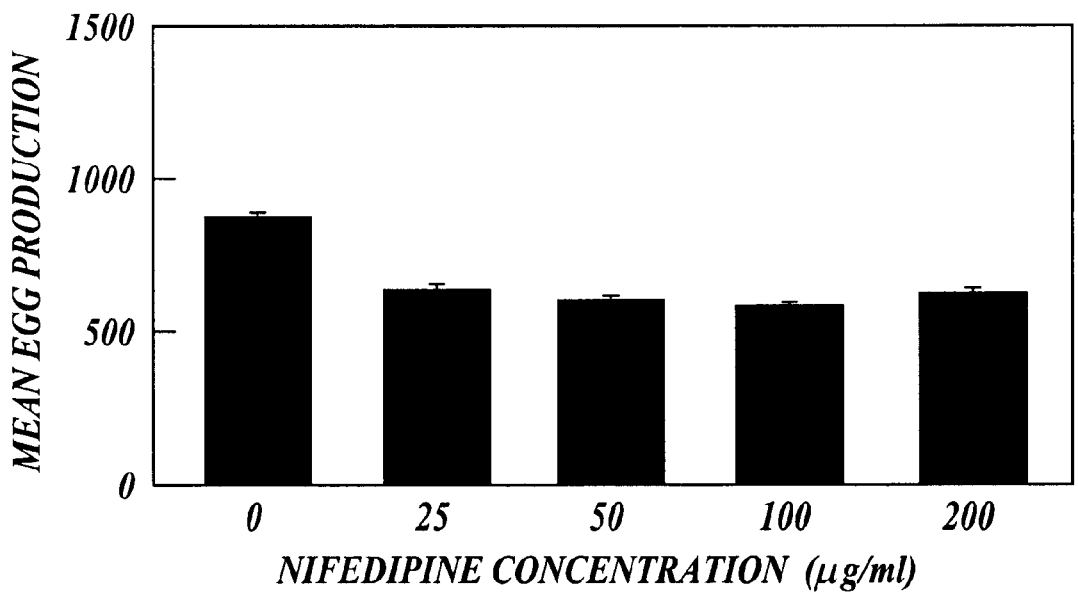
FIGS. 2A and 2B depict the effect of elevated (FIG. 2A) and therapeutic (FIG. 2B) concentrations of nifedipine on mean egg production of Echinostoma caproni as compared to controls.

All worms were alive and exhibited normal flexing movement after 24 hours in culture. Further, no sloughing of the tegument was apparent. Elevated concentrations of verapamil and nifedipine significantly inhibited production of eggs by *Echinostoma caproni* compared to worms in control treatments (FIGS. 1A and 2A). No concentration-dependent effects were associated with the verapamil treatment as evidenced by a lack of significant pairwise differences among the concentrations. In contrast, not all concentrations of nifedipine were effective. Specifically, the lowest concentration of nifedipine (25 µg/ml) did not significantly inhibit egg production (FIG. 2A).

Figure 3A:
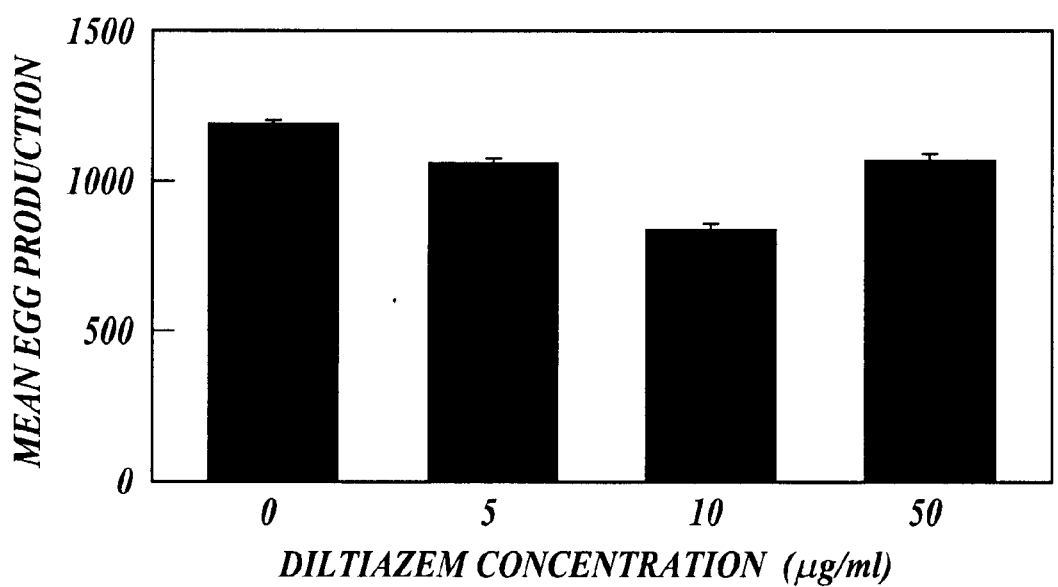
FIGS. 3A and 3B depict the effect of elevated (FIG. 3A) and therapeutic (FIG. 3B) concentrations of diltiazem on mean egg production of Echinostoma caproni as compared to controls.

Diltiazem did not significantly inhibit egg production despite using a concentration range about 10 to 100 fold greater than the normal effective therapeutic range in mammals (FIG. 3A). Further, there were no significant pairwise differences among concentrations (5 to 50 µg/ml).

Figure 1B:
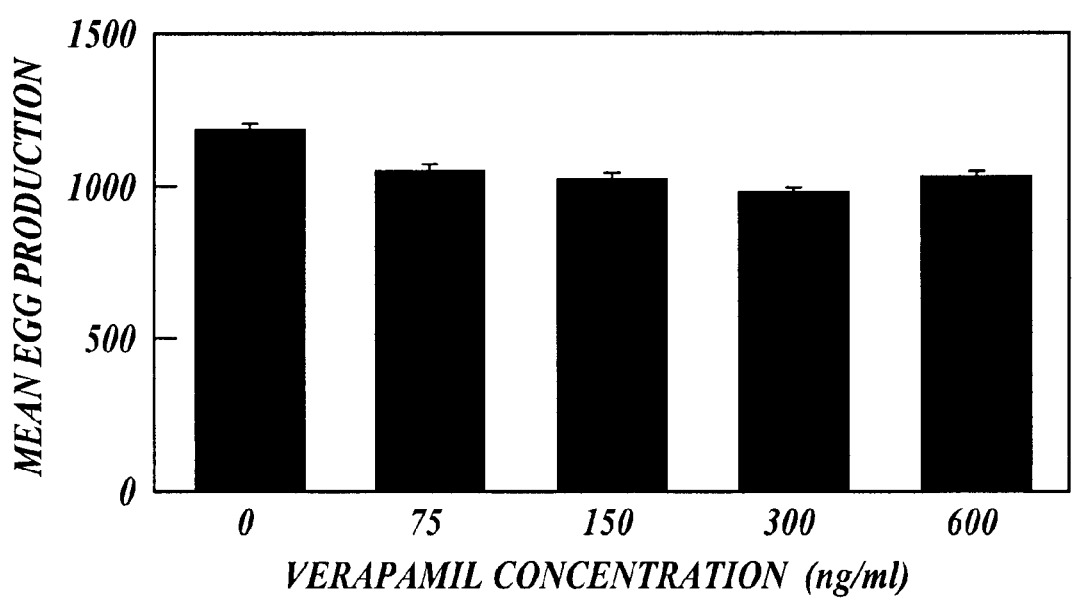
Figure 2B:
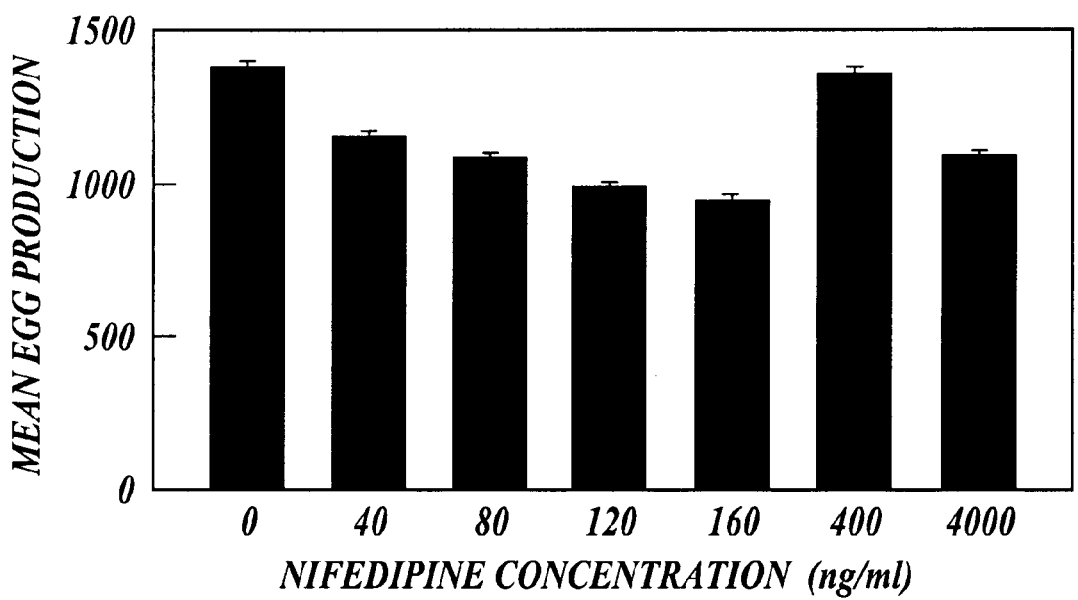
Figure 3B:
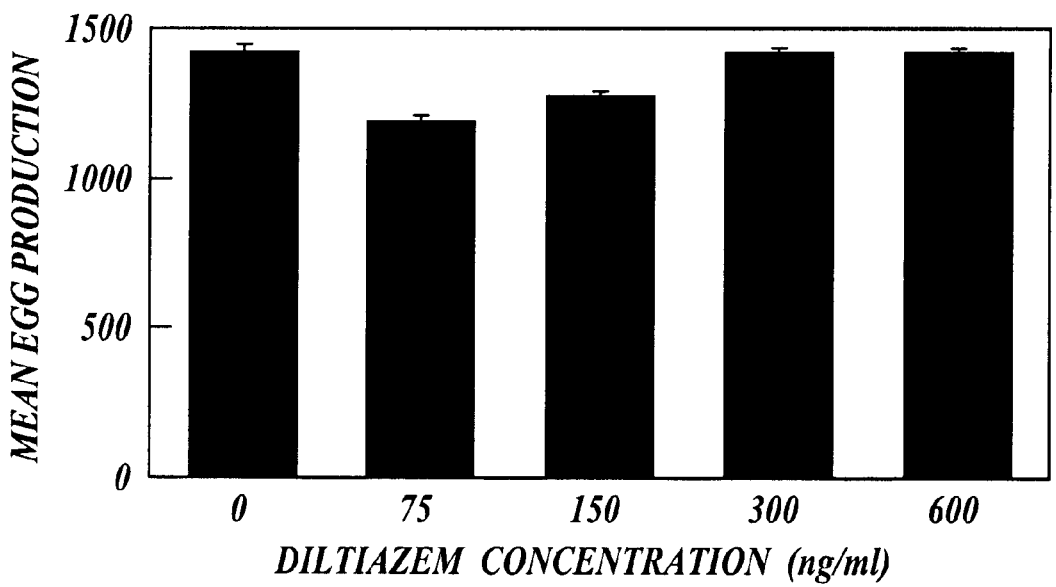

When used in therapeutic concentrations, none of the three calcium channel blockers significantly inhibited *E. caproni* egg production (FIG. 1B, FIG. 2B, and FIG. 3B). However, efficacy of nifedipine approached significant levels (p=0.09).

In spite of the variations in the effectiveness of the various calcium channel blocking agents in reducing egg production, the analysis of the above data demonstrates that the representative phenylalkylamine, verapamil, and the representative dihydropyridine, nifedipine, significantly inhibited egg production by *E. caproni*. Hence *E. caproni* possesses binding sites for verapamil and nifedipine. However, this effect required concentrations above the concentration of the drugs demonstrated to be therapeutic for cardiovascular disease in humans. The requirement for "high" concentrations of these two drugs might be viewed as problematic because, in some systems, elevated concentrations of dihydropyridines have been found to block sodium channels in addition to blocking calcium channels (Yatani et al., *Am. J. Physiol.* 254:H140-H147 (1988). However, the trend toward significant inhibition of egg production in the presence of therapeutic concentrations of nifedipine argues against the involvement of sodium, as these concentrations would normally be insufficient to give rise to sodium blockade. Further, elevated concentrations of verapamil are not known to block sodium channels and yet were highly efficacious in inhibiting egg production indicating that sodium influx does not contribute to the inhibitory activity of verapamil. Taken together, these results demonstrate that calcium influx is intimately involved in the regulation of *E. caproni* egg production.

Importantly, the inhibitory activities of verapamil and nifedipine were directed against de novo egg production. Preliminary investigations demonstrated that worms removed from mice and dissected immediately, contained an average of approximately 300 eggs, whereas the mean egg production observed in control groups was always substantially greater than this after 24 hrs in culture (infra). Further, Reddy and Fried (*Parasit. Res.* 82:475–476 (1996)), using similar culture conditions, demonstrated that de novo egg production occurred during 24 hour cultures of *E. caproni*, and represented approximately two-thirds of the total eggs recovered. Hence, de novo egg production occurs in *E. caproni* during short (24 hour) in vitro culture periods, and is inhibited by calcium channel blockade.

In contrast to the efficacy of nifedipine and verapamil, egg production was not significantly affected by diltiazem at the concentrations tested. This result is not surprising since the affinity of calcium channels for transient blocking agents varies with the specific channel blocker, the target tissue and/or the species of organism. Accordingly, the calcium channels of *E. caproni* either do not possess binding sites for, or possess sites of lower affinity for, diltiazem.

Although the efficacies of the three calcium channel blocking agents differed, *E. caproni* egg production was inhibited by calcium channel blockade, indicating the egg production process requires influx of extracellular calcium. Further, the sensitivity of *E. caproni* to two of the calcium channel blockers argues that L-type calcium channels exist on membranous surfaces accessible to exogenous drugs. Such externally directed binding sites would be accessible to orally administered compounds and represent targets for the development of novel anti-helminthic therapies against trematodes whose eggs are a significant cause of pathology.

EXAMPLE 2

In this example *Schistosoma mansoni* were treated with verapamil at 0.25, 2.5 and 50 µg/ml. $Ca^{++}$ was present in the culture medium at about 1.0 mM (about 2 to 4 times $K_i$). The mean number of eggs produced by a worm were determined for each worm isolated at various time points during culture.

Briefly, sufficient drug stock was made up in an appropriate solvent and added to 100 ml of culture medium (RPMI 1640, 8% fetal calf serum) to give the final desired concentration. Swiss Webster mice were infected with approximately 200 cercariae of a Puerto Rican strain of *Schistosoma mansoni* (Biomedical Research Institute, Baltimore, Md.). Mice were group housed and fed and watered ad libitum. At approximately 8 weeks post infection the mice were euthanized with a pentobarbital/heparin mixture. Adult worms were recovered by perfusion of the liver vasculature with buffered saline (Duvall and DeWitt, *Am. J. Trop. Med. Hyg.* 16:483–486 (1967)). The isolated worms were washed multiple times in sterile RPMI 1640, pH 7.4 (Sigma).

Parasites were cultured in 24 well culture plates (Falcon) in 5 ml/well of culture medium comprising of RPMI-1640 supplemented with 8% fetal calf serum (GIBCO), 100 U/ml penicillin (Sigma), 100 µg/ml streptomycin (Fisher), and appropriate volumes of stock verapamil hydrochloride (Sigma) solubilized in culture medium to give final concentrations of 0.25, 2.5, or 50 µg/ml drug. Controls received culture medium only.

The drug concentrations were chosen based on the clinically relevant range of maximum steady-state plasma concentrations ($C_{max}$) for verapamil. Concentrations of drug within (0.25 µg/ml), slightly higher (2.5 µg/ml) and multiply-fold greater (50 µg/ml) than $C_{max}$ were used to ensure a response would not be missed due to insufficient range of drug. Additionally, the calcium concentration of the culture medium was approximately 0.6 to 1.0 mM, which is approximately 2 to 3 fold greater than the concentration of calcium (about 0.3 mM) required for 50% inhibition ($K_i$) of verapamil binding to L channels of isolated skeletal muscle (Galizzi et al., *Eur. J. Biochem.* 144:211–215 (1984)). Excess calcium was not chelated biasing the experimental design against drug efficacy.

Seven plates were prepared, and one worm pair (one male and one female worm) were placed in each well of the plates. Each row of six wells constituted a single treatment (i.e., concentration), giving a total of 42 worm pairs per treatment group. Groups were randomized by sequentially rotating their row assignment through seven plates, and by randomly assigning plates to an initial position within the incubator and rotating the position of each plate in the incubator each day of incubation. Cultures were incubated at 37° C. in 95% air/5% $CO_2$ for eight days with the medium changed daily. The cultures were examined daily using an inverted microscope to assess viability of worms and to determine the first day on which eggs were oviposited.

Figure 4:
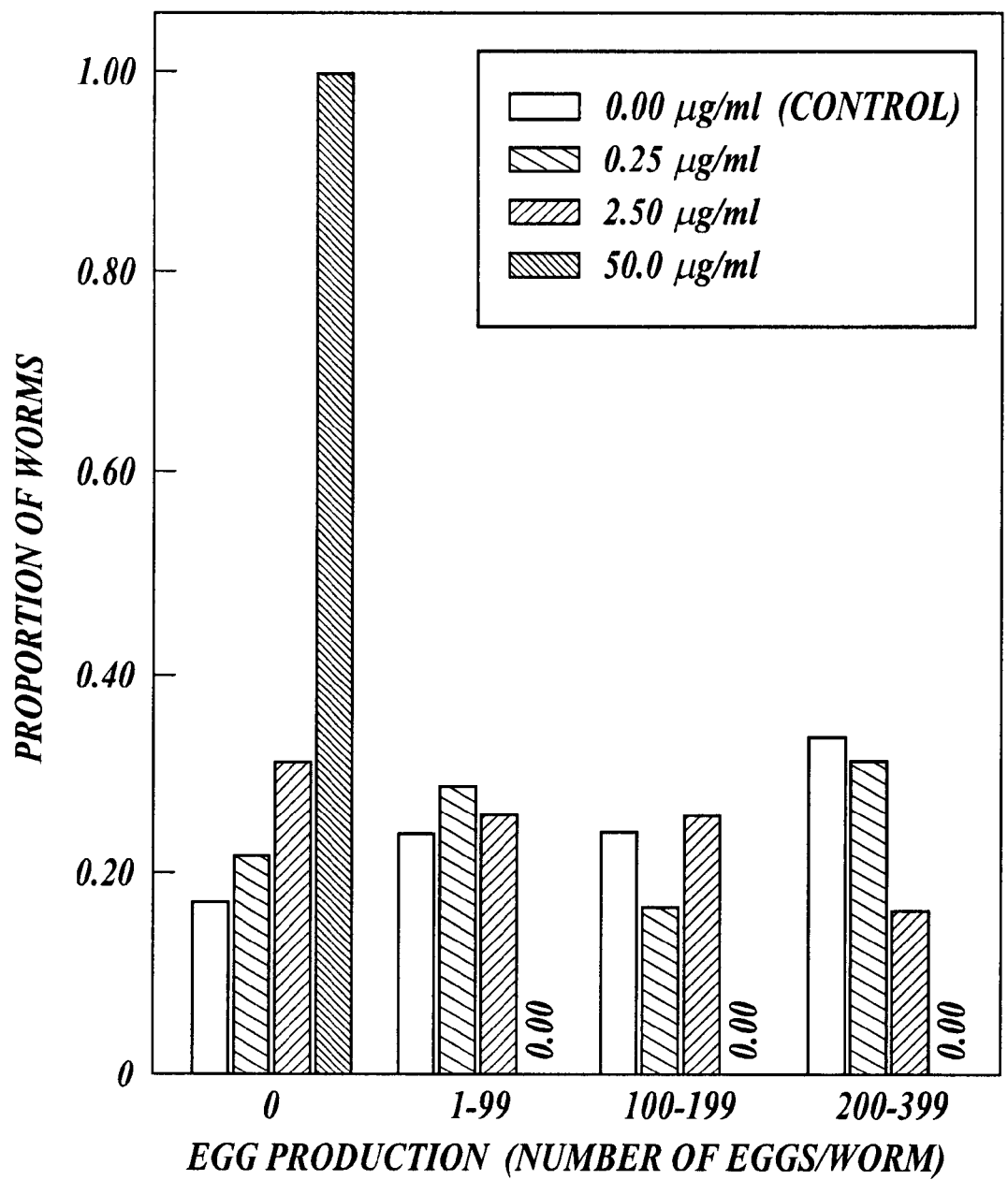
FIG. 4 depicts the effect of various concentrations of verapamil on Schistosoma mansoni egg production.

After eight days of incubation, all plates were removed and the viability of all worms was again assessed visually. Worms were then removed and morphologically "normal" eggs were counted. Misshapen and/or spineless eggs, and egg shell debris, were not included in the egg counts. Egg production by control and drug-treated worms was divided into four categories: 0, 1–99, 100–199 and 200–399 eggs/worm (FIG. 4). Differences in overall egg production and the proportion of non-producers among all treatment groups were analyzed by the Chi Square test. Where significant overall differences were observed, pairwise comparisons of control and treatment groups were done using the Fisher Exact test (2-tailed). Differences in the time to egg production were analyzed by determining the number of worms for which the first recorded appearance of eggs occurred a) within 48 hrs of culture and b) after 48 hrs of culture for each treatment group (Table 1), and comparing each treatment with the control using the Fisher Exact Test. The 50 μg/ml verapamil group was not included in this analysis as no eggs were produced at any time.

Results

The effect of verapamil on egg production was significant when all treatments were analyzed together (Chi Square= 82.59, p=0.001). In order to define the way in which verapamil effected this overall inhibition of egg production, drug-associated changes in the proportion of worms producing no eggs (non-producers) and those producing eggs (producers) were analyzed. Verapamil significantly affected the proportion of non-producers when analyzed across all treatments (Chi Square=77.23, p=0.001). However, pairwise comparisons showed that only the 50 μg verapamil treatment significantly affected egg production (Fisher Exact test, 2-tailed, p<0.0001).

The lack of efficacy of the 0.25 μg/ml and 2.5 μg/ml verapamil treatments extended to egg-producing worms. Treatment with these concentrations did not significantly affect the proportion of worms producing eggs in the three production categories analyzed; 1–99 eggs/worm, 100–199 eggs/worm, and 200–399 eggs/worm (FIG. 4, Chi Square 4.15, p=0.386). However, there was an apparent trend towards inhibition mediated by 2.5 μg/ml verapamil in the highest egg-production category (100–399 eggs/worm). Only 15% of worms treated with this concentration of drug fell into this highest production category, compared to 34% of control worms (FIG. 4).

In contrast to the lack of efficacy of the 0.25 μg/ml and 2.5 μg/ml verapamil treatments with respect to schistosome egg production, the time required to initiate production was significantly increased by verapamil when analyzed across these treatments (Chi Square=8.216, p=0.016). However, pairwise comparisons showed that 2.5 μg/ml, but not 0.25 μg/ml, verapamil significantly increased the proportion of worms which did not produce eggs until after 48 hours of culture (Fisher's exact test, 2-tailed, p=0.013).

Importantly, to restrict analysis of drug effects to worms which were apparently healthy, all worms were visually assessed for viability upon conclusion of the experiment. Only two worms (out of 336) appeared moribund or dead by the end of the experiment, and these were dropped from the data analysis. All remaining worms were actively flexing and showed no apparent tegumental damage or sloughing upon visual assessment.

TABLE 1

Affect of Verapamil on Time to Egg Production

| Verapamil (μg/ml) | 48 Hours* | 48+ Hours |
|---|---|---|
| 0 | 28 | 6 |
| 0.25 | 24 | 8 |
| 2.5 | 14 | 14 |
| 50 | 0 | 0 |

*= number of worms producing eggs within time category given

Verapamil typifies the phenylalkylamine class of calcium channel blocker (CCB). At clinically relevant levels verapamil for cardiovascular disease demonstrates specificity for L-type calcium channels (Hosey and Lazdunski, *J. Mem. Biol.* 104:81–105 (1988)). As is true for nearly all CCBs of the three useful classes (benzothiazepines, dihydropyridines, phenylalkylamines), the binding of verapamil to the L-channel and its consequent activity is inhibited by high concentrations of calcium (Galizzi et al., *Eur. J. Biochem.* 144:211–215 (1984)). This pharmacokinetic (binding) profile of verapamil may partly explain why the overall effect of 50 μg/ml verapamil on egg production was significant while the effects of 0.25 μg/ml and 2.5 μg/ml verapamil were not. As the concentration of calcium in the culture medium was a minimum 2 to 3 fold greater than the $K_i$, the activity of 0.25 μg/ml verapamil was likely completely inhibited by the available calcium.

While inhibition of a therapeutic concentration of verapamil is understandable in this light, the activity of 2.5 μg/ml, a concentration 5 to 10 times the $C_{max}$, was also apparently inhibited by the concentration of external calcium. In this instance, although the high calcium likely decreased drug binding and thus the magnitude of its activity, the results can also indicate a relatively low affinity of the schistosome calcium channels for verapamil. This interpretation was supported by the effect obtained with 50 μg/ml verapamil, a concentration high enough to mediate substantial blockade of channels with low affinity binding sites which completely eliminated egg production. Further, support was lent by the substantial inhibitory effect of 2.5 μg/ml verapamil on high rates of egg production. Such high egg output would presumably require greater calcium influx than lower rates of production. If so, even low affinity binding of verapamil could potentially block sufficient calcium to inhibit this level of egg production. In contrast, lesser levels of production would not be as vulnerable to such a low degree of blockade due to a much lower calcium requirement.

Although the overall effects of 0.25 μg/ml and 2.5 μg/ml verapamil were not statistically significant, certain aspects of egg production were substantially influenced by drug treatment. The proportion of non-producers was nearly doubled by 25 μg/ml verapamil (30%) relative to control worms (17%). In addition, treatment with this concentration of drug decreased by half the proportion of worms competent to produce eggs and those producing large numbers of eggs could correspondingly decrease the intensity-dependent pathology in vivo, even without removal of adult parasites.

It should also be noted, that the time required to initiate egg production was significantly delayed by treatment with 2.5 μg/ml verapamil. Because there is a narrow window (days 1–4 of culture) for maximal egg production by schistosomes under culture conditions (el Ridi et al., *Int. J. Parasitol.* 27:381–387 (1997), a drug-induced temporal delay could have brought about other effects (e.g., an increase in non-producers, decrease in heavy-producers, and the like) of the 2.5 µg/ml treatment by shifting a proportion of the worm "population" beyond the critical production period.

The pathology of schistosomiasis is complex, and results from the interaction of multiple factors, including worm burden, parasite fecundity, the accumulated egg burden over time, and the immunological response of the host (Cheever et al., *Am. J. Trop. Med. Hyg.* 26:702–716 (1977), von Lichtenberg et al., *Am. J Trop. Med. Hyg.* 20:850–893 (1971), von Lichtenberg, in, *The Biology of Schistosomes: From Genes to Latrines,* Rollinson and Simpson eds. Academic Press, pp 185–224 (1987), Warren, *Nature* 273:609–612 (1978)). Thus, the total number of eggs produced by all worms in each treatment group was used as a proxy measure of the accumulated egg burden of the in vitro "population." The 50 µg/ml and 2.5 µg/ml verapamil treatments effected respective decreases in the total number of eggs produced of 100% and 38%. Hence, when the in vitro schistosome "population" is considered, verapamil demonstrated substantial inhibitory activity even in the presence of excess calcium.

Taken together, the above results indicate that *Schistosoma mansoni* possesses calcium channels sensitive in some degree to phenylalkylamine blockade. Because the affinity and efficacy of calcium channel blockers has been determined to be variable within and between organisms, testing with other calcium channel blockers would be expected to provide similar effects and only sone testing must be performed to determine to which agents Schistosoma species are most sensitive. Further, the above data suggests that calcium channel blockers can provide a novel means of interrupting schistosome reproduction and consequent pathogenesis and transmission.

While specific examples have been provided, the examples and description provided is illustrative and not restrictive. Many variations of the invention will become apparent to those skilled in the art upon review of this specification. The scope of the invention should, therefore, be determined not with reference to the description provided, but instead should be determined with reference to the appended claims along with their full scope of equivalents. All publications and patent documents cited in this application are incorporated by reference in their entirety for all purposes to the same extent as if each individual publication or patent document were so individually denoted.

What is claimed is:

1. A method for inhibiting egg production in a trematode worm by administering to an individual in need thereof a therapeutically or prophylactically effective amount of an agent which transiently inhibits calcium influx through a cell membrane calcium channel.

2. The method of claim 1, wherein the calcium channel is an L type calcium channel.

3. The method of 1, wherein the agent comprises a dihydropyridine, a phenylalkylamine, a benzothiazepine, a diphenylbutylpiperidine, or a flunarizine/cinnarizine series compound.

4. The method of claim 1, wherein the dihydropyridine comprises nifedipine (1,4-dihydro-2,6-dimethyl-4-(2-nitrophenyl)-3,5-pyridinedicarboxylic acid dimethylester).

5. The method of claim 3, wherein the phenylalkylamine is verapamil (α-[3-[[2-(3,4-dimethoxyphenyl)ethyl]methylamine]propyl]-3,4-dimethoxy-α-(1-methylethyl)-benzeneacetonitrile).

6. The method of claim 3, wherein the benzothiazepine comprises diltiazem (3,4,5-trimethoxybenzoic acid (tetrahydro-1H- 1,4-diazepine-1,4(5H)-diyl)di-3,1-propanediyl ester).

7. The method of claim 3, wherein the diphenylbutylpiperidine comprises pimozide (1-[1-[4,4-bis(4-fluorophenyl)butyl]-4-piperidinyl]-1,3-dihydro-2H-benzimidazol-2-one), or fluspirilene (8-[4,4-bis(4-fluorophenyl)butyl]-1-phenyl-1,3,8-trizaspiro[4.5]decan-4-one).

8. The method of claim 3, wherein the flunarizine/cinnarizine series compound comprises a flunarizine ((E)-1-[bis(4-fluorophenyl)methyl]-4-(3-phenyl-2-propenyl)piperazine) or a cinnarizine (1-(diphenylmethyl)-4-(3-phenyl-2-propenyl)piperazine).

9. The method of claim 1, wherein the trematode worm is a schistosome or an echinostome worm.

10. The method of claim 9, wherein the schistosome worm is *Schistosoma mansoni*.

11. The method of claim 9, wherein the Echinostoma worm is *Echinostoma caproni*.

12. The method of claim 1, wherein the effective amount of the agent comprises a $C_{max}$ of no more than about 500 ng/ml.

13. The method of claim 12, wherein the effective amount of the agent produces a $C_{max}$ of about 30 ng/ml to about 500 ng/ml.

14. The method of claim 12, wherein the effective amount of the agent produces a $C_{max}$ of about 30 ng/ml to about 150 ng/ml.

* * * * *